US012758476B2

(12) United States Patent
Cox

(10) Patent No.: US 12,758,476 B2
(45) Date of Patent: Oct. 13, 2026

(54) ACID RESISTANT COMPOSITION HAVING IMPROVED SOLUBILITY

(71) Applicant: Jeffrey S. Cox, Fenton, MI (US)

(72) Inventor: Jeffrey S. Cox, Fenton, MI (US)

( * ) Notice: Subject to any disclaimer, the term of this patent is extended or adjusted under 35 U.S.C. 154(b) by 66 days.

(21) Appl. No.: 17/831,413

(22) Filed: Jun. 2, 2022

(65) Prior Publication Data

US 2022/0401323 A1 Dec. 22, 2022

Related U.S. Application Data

(60) Provisional application No. 63/196,100, filed on Jun. 2, 2021.

(51) Int. Cl.

| | |
|---|---|
| ***A61K 8/362*** | (2006.01) |
| ***A61K 6/35*** | (2020.01) |
| ***A61K 6/50*** | (2020.01) |
| ***A61K 8/19*** | (2006.01) |
| ***A61Q 11/00*** | (2006.01) |

(52) U.S. Cl.

CPC ................ *A61K 8/362* (2013.01); *A61K 6/35* (2020.01); *A61K 6/50* (2020.01); *A61K 8/19* (2013.01); *A61Q 11/00* (2013.01)

(58) Field of Classification Search

CPC ........... A61K 8/362; A61K 8/02; A61Q 11/00

USPC .................................................... 424/49, 401

See application file for complete search history.

(56) References Cited

U.S. PATENT DOCUMENTS 9,717,665 B2 * 8/2017 Sagel ..................... A61Q 11/00

FOREIGN PATENT DOCUMENTS

| | | | |
|---|---|---|---|
| RU | 2670432 * | 10/2018 | ............. A61K 8/362 |
| WO | WO-0048562 A1 * | 8/2000 | ............. A61K 6/002 |
| WO | WO2015140308 * | 9/2015 | ............. A61K 33/10 |

OTHER PUBLICATIONS

Knowde, "VYNOVA Renewable Caustic Soda." www.knowde.com/stores/vynova/products/vynova-renewable-caustic-soda. Published online Apr. 14, 2021 (Year: 2021).*

* cited by examiner

*Primary Examiner* — Walter E Webb

(74) *Attorney, Agent, or Firm* — Lawrence C. Begin

(57) ABSTRACT

Dental desensitizing solutions and methods of using the solutions are disclosed. The solution may include an active ingredient, the active ingredient, when applied to a tooth, being configured to react with calcium in the tooth to produce a plurality of acid-resistant crystals that at least partially occlude dentinal tubules in the tooth. The solution may include a solubility enhancer, the solubility enhancer increasing the solubility of the active ingredient in the solution. The active ingredient may be oxalic acid, potassium salt dihydrate and the solubility enhancer may be sodium hydroxide, however, other active ingredients and solubility enhancers are disclosed. The solution may be applied to the tooth dentin and/or cementum to reduce hypersensitivity or pain from certain stimuli. The solution may increase the solubility of the active ingredient by at least 1.0 g/L at a given temperature. The solution may include at least 0.3 g/L of the solubility enhancer.

28 Claims, 14 Drawing Sheets

FIG 22

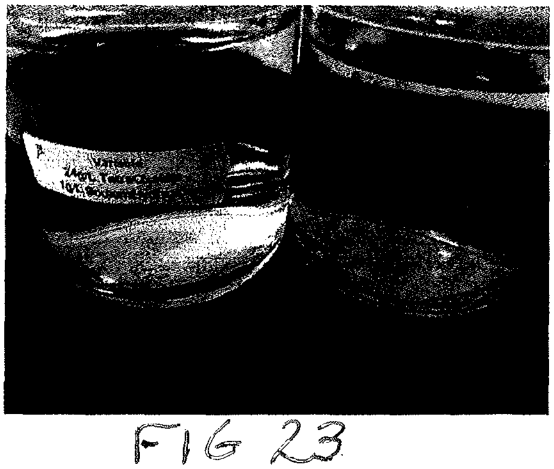

FIG 23

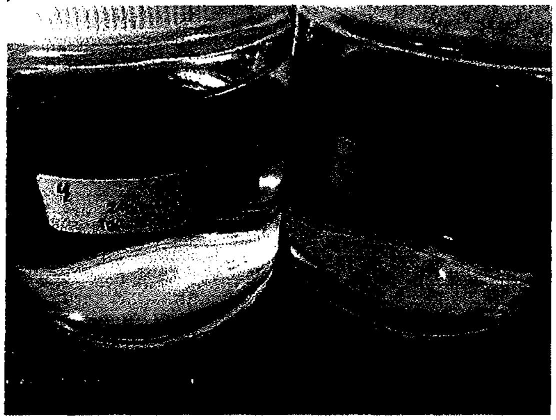

FIG 24

| Testing start time | 8/28/14 10:00 AM |
|---|---|

| | | END POINT REACHED | | | | |
|---|---|---|---|---|---|---|
| | | α | β | ε | γ | μ |
| NaOH | Variable | 8/29/14 9:00 AM | 8/29/14 9:00 AM | 9/2/14 9:20 AM | 9/2/14 9:20 AM | 8/29/14 9:00 AM |
| Non-NaOH | Control | 9/8/14 9:20 AM | 9/8/14 9:20 AM | 9/5/14 11:20 AM | 9/5/14 11:20 AM | 9/8/14 9:20 AM |

| | | Hours Data | | | | |
|---|---|---|---|---|---|---|
| | | α | β | ε | γ | μ |
| NaOH | Variable | 23 | 23 | 23 | 23 | 23 |
| Non -NaOH | Control | 23 | 23 | 1 | 1 | 23 |

| | | Days Data | | | | |
|---|---|---|---|---|---|---|
| | | α | β | ε | γ | μ |
| NaOH | Variable | 0 | 0 | 4 | 4 | 0 |
| Non -NaOH | Control | 10 | 10 | 8 | 8 | 10 |

| | | Total Hours Elapsed to Reach Endpoint | | | | |
|---|---|---|---|---|---|---|
| | | α | β | ε | γ | μ |
| NaOH | Variable | 23 | 23 | 119 | 119 | 23 |
| Non -NaOH | Control | 263 | 263 | 193 | 193 | 263 |

| | | Average Hours Elapsed to Endpoint | Average Hour Difference Control -Variable |
|---|---|---|---|
| NaOH | Variable | 61.4 | 173.6 |
| Non -NaOH | Control | 235 | |

FIG. 25

ACID RESISTANT COMPOSITION HAVING IMPROVED SOLUBILITY

CROSS-REFERENCE TO RELATED APPLICATIONS

This application claims the benefit of U.S. Provisional Application Ser. No. 63/196,100 having a filing date of Jun. 2, 2021, the contents of which are hereby fully incorporated by reference.

TECHNICAL FIELD

The present disclosure relates to an acid resistant composition having improved solubility, for example, for use in dental applications.

BACKGROUND

Individuals often report an immediate increase in hypersensitivity or pain when exposed certain stimuli (e.g., sudden extremes of thermal stimuli), either in a particular tooth or a group of teeth. This may occur following a replacement or a restoration, the initial placement of an existing amalgam alloy or a tooth-colored resin composite restorations, or following the bleaching of teeth with power (light, heat or other) assisted forms of tooth whitening systems. The dentist may simply caution patients to be aware of an immediate increased feeling of pain to a rapid jet of air, cold drinks, to chewing forces of occlusion, or to other factors such as acidic foods. Stimuli, such as cold water, cool air, osmotic gradient shifts, or sweet or acidic solutions at the cavosurface margin of a restoration have all been shown to cause an immediate increase in the dentin pain response. Dentists may simply call this phenomenon patient dentin pain (postoperative hypersensitivity/DPH) or simply dental discomfort. Often the dentist tells patients to simply wait a few days or weeks and that the pain of discomfort will become less and less, and eventually that it should go away.

The acute, sharp, piercing pain of dentin pain is often a fairly common complaint among many patients who have recently received an amalgam alloy or resin composite restoration in vital dentin that has been treated with a conventional dentin liner such as a calcium hydroxide $Ca(OH)_2$ material, such as Dycal® or Life®. Dentin postoperative hypersensitivity generally occurs with the normal physiological breakdown of the smear layer or its removal at the cavosurface margin due to oral fluids which reach an acidic pH of 2.7 to more neutral at pH of 6.0.

If the dentist uses any type of instrumentation, for example, rotary instrumentation with a drill or bur or scraping or polishing with any sort of hand instrument, it will leave a layer of debris on the tooth surface called a smear layer. The breakdown of the smear layer by physiological action, or by the dentist, opens and exposes the dentinal tubule complex to a bi-directional flow of fluids from the dental pulp. It is this increased bi-directional fluid flow which is responsible for the patients' dentin postoperative hypersensitivity to cold or rapid air flow.

The physiological mechanism for dentin pain following placement of either an amalgam alloy or a resin composite restoration has been explained as being due to the breakdown or loss of the smear layer which then results in an immediate increased flow of pulpal fluids though its micro channel complex. This increase in flow may be 94% greater than the normal physiological flow of fluids through the normal dentin substrate.

SUMMARY

In at least one embodiment, a dental desensitizing solution is provided. The solution may include an active ingredient, the active ingredient, when applied to a tooth, being configured to react with calcium in the tooth to produce a plurality of acid-resistant crystals that at least partially occlude dentinal tubules in the tooth. The solution may include a solubility enhancer including sodium hydroxide (NaOH), the solubility enhancer increasing the solubility of the active ingredient in the solution.

The active ingredient may include an oxalic acid potassium salt. In one embodiment, the oxalic acid potassium salt includes oxalic acid, potassium salt dihydrate. The solubility enhancer may increase the solubility of the active ingredient by at least 1.0 g/L at a given temperature. In one embodiment, the solution includes at least 0.3 g/L of NaOH. A pH of the solution may be from 1.0 to 5.0. The solution may include from 0.1 to 6.0 g/L of the solubility enhancer. The solution may be an aqueous solution.

In one embodiment, the active ingredient may include one or more of: 2-hydroxypropanedioic acid; 2-oxopropanedioic acid; [(2-azanidylcyclohexyl) azanide; oxalic acid; platinum $(2^+)$]—(CID 24197462); [tripotassium; chromium$(3^+)$; oxalate; trihydrate (3:1:3:3)]—(CID 131874172); [tripotassium; chromium$(3^+)$; oxalate (3:1:3)]; tripotassium; 2-bis [(carboxylatoformyl)oxy]stibanyloxy-2-oxoacetate; and Oxotitanium $(2^+)$ potassium ethanedioate hydrate (1:2:2:2).

In at least one embodiment, a method of decreasing tooth sensitivity is provided. The method may include applying a solution including an active ingredient and a solubility enhancer including sodium hydroxide (NaOH) to the tooth, the active ingredient being configured to react with calcium in the tooth to produce a plurality of acid-resistant crystals that at least partially occlude dentinal tubules in the tooth. The solubility enhancer may be configured to increase the solubility of the active ingredient in the solution.

The solution may be applied to at least one of the tooth dentin and cementum. The active ingredient may include an oxalic acid potassium salt. In one embodiment, the oxalic acid potassium salt includes oxalic acid, potassium salt dihydrate. The solubility enhancer may increase the solubility of the active ingredient to at least 26 g/L at 20° C.

In at least one embodiment, a dental desensitizing solution is provided including an oxalic acid, potassium salt dihydrate; and a solubility enhancer. The solubility enhancer may increase the solubility of the oxalic acid, potassium salt dihydrate in the solution to at least 26 g/L at 20° C.

The solubility enhancer may include NaOH, KOH, LiOH, CsOH, RbOH, $Sr(OH)_2$, $Mg(OH)_2$, $Ba(OH)_2$, or mixtures thereof. Stated another way, the solubility enhancer may include alkali metal hydroxides, alkaline earth metal hydroxides, and/or mixtures thereof. The solution may include at least 0.3 g/L of the solubility enhancer. A pH of the solution may be from 1.0 to 5.0. In one embodiment, the solution includes 0.3 to 1.5 g/L of the solubility enhancer. The solubility enhancer may increase the solubility of the oxalic acid, potassium salt dihydrate to at least 28 g/L at 20° C., to greater than 25 g/L.

BRIEF DESCRIPTION OF THE DRAWINGS

FIG. 22 is the alpha samples after 11 days at room temperature;

FIG. 23 is the beta samples after 11 days at room temperature;

FIG. 24 is the mu samples after 11 days at room temperature;

FIG. 25 is a table of the results from FIGS. 2-24;

DETAILED DESCRIPTION

Figure 1:
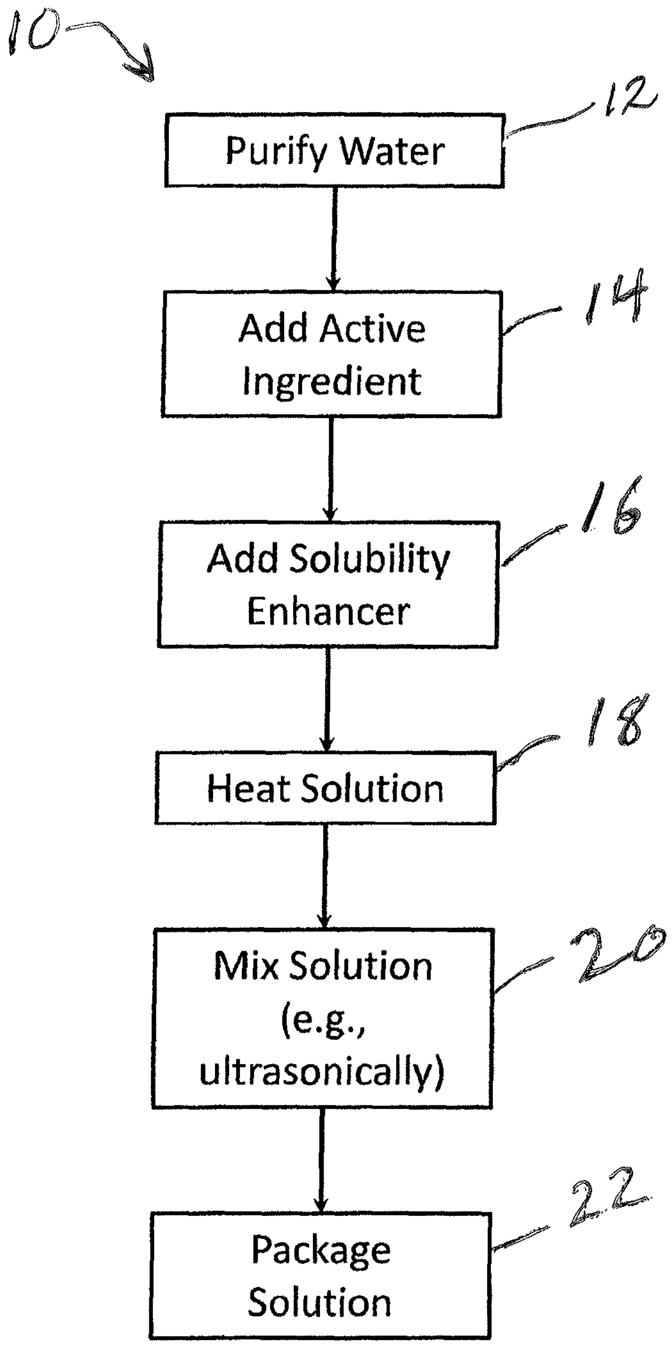
FIG. 1 is a flowchart of a method of forming an acid resistant composition with increased solubility, according to an embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The present disclosure relates to the use of an acid resistant composition that reacts with materials in the patient's mouth to occlude (e.g., physically) the dentinal tubules and decrease dentinal sensitivity, acid penetration, and discomfort. As described above, it is believed that bi-directional fluid flow is responsible for patients' dentin postoperative hypersensitivity to cold or rapid air flow. This is explained by Brännström's widely accepted hydrodynamic theory, which suggests that dentine hypersensitivity is due to movement of fluid within the dentinal tubules in response to mechanical, osmotic, and evaporative stimuli. In contrast to conventional approaches, the disclosed composition may utilize an active ingredient which, when applied to the surface of the tooth, penetrates into the tubules and fibrils of the dentin layer, and reacts with materials therein to form a physical barrier. In one embodiment, the active ingredient is a specific oxalic acid salt, oxalic acid, potassium salt dihydrate. The oxalic acid, potassium salt dihydrate, or it may be referred to as potassium oxalate dihydrate or potassium tetraoxalate dihydrate, eliminates fluid movement within the tubules and therefore renders the dentin incapable of transmitting painful stimuli to the pulp in the form of fluid movement. Therefore, no pain or discomfort is felt by the patient for long periods of time. Oxalic acid, potassium salt dihydrate is described in U.S. Pat. No. 6,423,301, the disclosure of which is hereby incorporated in its entirety by reference herein.

In at least one embodiment, the active ingredient of the disclosed composition is oxalate acid, potassium salt dihydrate 99% with a molecular weight of 254.19 and a formula of $C_4H_3KO_8 \cdot 2H_2O$ or $KH_3(C_2O_4)_2 \cdot 2H_2O$. While the active ingredient is described herein as oxalate acid, potassium salt dihydrate, a non-hydrated composition may also be used (e.g., $C_4H_3KO_8 \cdot 2H_2O$ or $KH_3(C_2O_4)_2$). Accordingly, unless otherwise stated, the non-hydrated composition may be substituted for the dihydrate composition. The oxalate potassium salt, dihydrate 99%, which is also referred to herein as potassium oxalate dihydrate, is a white crystalline powder that has a solubility in water of 25.419 g/L at 20° C. The potassium oxalate dihydrate may be utilized in an aqueous solution, which may include a gelatinous or gel-like solution. Dissolving the potassium oxalate dihydrate in water may be difficult using conventional practices. It has been found that subjecting a solution of potassium oxalate dihydrate to ultrasonic frequencies may help disperse the large crystals of the potassium oxalate in water and therefore increase the solubility in water.

While the disclosed composition is described with oxalic acid, potassium salt dihydrate (and its synonyms) as an example of the active ingredient, other active ingredients may also be used. In addition, the active ingredient may include one or more of the following disclosed compounds or compositions. The following table includes compounds or compositions that may be included in the active ingredient:

TABLE 1

| Name | CAS Number | ChemSpider ID |
|---|---|---|
| 2-(carboxymethoxy)maloic acid | | 35763 |
| 2-(dicarboxymethoxy)propanedioic acid or Ditartronic Acid | | 84572 |
| Isomalic acid | | 120158 |
| Tartronate | | 43 |
| Tartronic Acid | 80-69-3 | 44 |
| Iminomalonate | | 24807310 |
| Mesoxalate | | 3399399 |
| Mesoxalic acid | 473-90-5 | 9727 |
| dipotassium [(carboxylatocarbonyl)oxy](oxo)titanio oxalate | | 17215158 |
| Tripotassium bis[(carboxylatocarbonyl)oxy]stibanyl oxalate | | 17616437 |
| Trisodium 2-(carboxymethoxy)propanedioic acid | | 35762 |
| (2-azanidylcyclohexyl)azanide; oxalic acid; platinum(2+) | 61758-77-8 | |
| 3-dexoyhexarate | | 1673 |
| dipotassium; oxalate; platinum(2+); dihydrate | 14244-64-5 | 141474 |
| tripotassium; chromium(3+); oxalate; hydrate (3:1:3:3) | 15275-09-9 | |
| tripotassium; chromium(3+); oxalate (3:1:3) | 15275-09-9 | |
| tripotassium;2-bis[(carboxylatoformyl)oxy]stibanyloxy-2-oxoacetate | 5965-33-3 (RN) | 4891125 |
| Potassium trioxalotoferrate (III) | 5936-11-8 | 8108406 |
| Potassium hydrogen ethanedioate zirconium (4:4:1) | | 17344854 |
| Potassium hydrogen ethanedioate hafnium (4:4:1) | | 17344856 |
| Oxotitanium (2+) potassium ethanedioate hydrate (1:2:2:2) | 14402-67-6 | |
| Dipotassium oxalate titanium (4+) (2:3:1) | 14481-26-6 | |
| dipotassium; dioxoosmium(2+); oxalate | 22827-17-4 | |
| Potassium chromium(III) oxalate trihydrate | 15275-09-9 | |
| Potassium titanium oxide oxalate dihydrate | 14402-67-6 | |
| tripotassium 2,2'2",-[stibinetriltris(oxy)]tris(oxoactate) | | 17616437 |
| tetra potassium tertrakis[ethanedioato(2-)-kO1]halfnium | | 21169920 |
| tetra potassium tertrakis[ethanedioato(2-)-kO1]zirconum | | 21169921 |
| Potassium hydrogen ethanedioate (1:3:2) | | 29125 |
| ethanedioate, potassium salt hydrate (1:1:2) | | 2006348 |
| potassium ethanedioate hydrate (4:2:1) | | 2006348 |
| potassium tetraoxalate | 127-96-8 | 21079 |
| potassium tetraoxalate dihydrate | 6100-20-5 | 2015875 |
| potassium trihydrogen dioxalate | 127-96-8 | 21079 |
| 2,3-dihydroxybutanedioic acid | 526-83-0 | 388726 |
| 2,3-dihydroxy-(2R,3R)-butanedioic acid monopotassium salt | 868-14-4 | 2006431 |
| potassium sodium tartrate | 304-59-6 | 145027 |
| dipotassium tartrate | 921-53-9 | 8636 |
| potassium sodium tartrate tetrahydrate | 6381-59-5 | 145027 |

Where known, the CAS Registry Number and/or the ChemSpider ID for the chemical compound has been provided. Certain compositions may be known by more than one name (synonyms). Some chemical synonyms have been provided in the table, however, any synonyms of the listed compositions not explicitly listed may also be used in the active ingredient. In addition, some compositions are listed as hydrated or non-hydrated. However, either the hydrated or non-hydrated composition may be included in the active ingredient.

A solution including the active ingredient (e.g., potassium tetraoxalate dihydrate) may be prepared using double distilled deionized water, with a water purity of 1,000,000 to 5,000,000 resistance in ohms, according to standardized testing of the American National Standards Institute. The high resistance equates to high purity. Other forms of purified water may be utilized; however, the double distilled deionized water is preferred in at least one embodiment. The active ingredient (e.g., oxalic acid potassium salt, dihydrate) may be added to the water such that the amount in the final solution ranges from 0.25% to 25.0% weight to volume (e.g., g/L), or any sub-range therein. For example, the active ingredient may be present in an amount from 0.25% to 20.0%, 0.25% to 15.0%, 0.25% to 10.0%, 0.25% to 7.5%, 0.5% to 7.5%, 0.5% to 5.0%, 0.75 to 7.5%, 0.75% to 5.0%, 1.0% to 7.5%, 1.0% to 5.0%, 1.0% to 4.0%, 1.5% to 3.5%, or 2.0% to 3.0%. The water and crystals may then be subjected to ultrasonic vibration, for example, variable ultra-high frequency wave action, to disintegrate the crystals into exceedingly small particles to form a solution. This may be accomplished using an ultrasonic cell disrupter; however, any means can be used to solubilize the active ingredient.

One suitable ultrasonic cell disruptor may be identified as the Branson Sonifier. The sonifier converts electrical energy from a power supply to mechanical vibration.

In one embodiment, the water and active ingredient (e.g., potassium oxalate dihydrate crystals) are placed in a mixing container and attached to a pumping system. The pump may circulate the water in a continuous flow at a certain flow rate (e.g., at about ½ liter per minute). The water and crystals may be circulated in the chamber for a certain length of time, such as about 30 minutes. The mechanical vibration from the sonifier may range from a frequency of about 16,000 Hz to about 40,000 Hz at the tip of the ultrasonic horn as it disrupts and disintegrates the crystals into very small particles so that they go into solution. For example, the frequency of vibration may be from 20,000 Hz to 30,000 Hz. During circulation, the water and crystal mixture may pass the ultrasonic horn multiple times, which continues to disintegrate the crystals into smaller particles each time it passes. The mean particle size in the final product may be from about 5 microns to about 15 microns when viewed under a 100-power microscope. After solubilization, no precipitate may be visible after 24 hours with the unaided human eye. Particle sizes outside of the range of about 5 microns to 15 microns may be suitable, depending on the amount of solute and/or the solubilization conditions. However, in one embodiment, the particle size is about 10 microns. In yet another embodiment, and particularly when an exemplary solubilizing agent such as sodium hydroxide is used, particles less than one micron in size may be produced thereby enhancing the depth to which the particles occlude the dentinal tubules. The combination of the novel solubility enhancer with the use of the sonifier dramatically improves the dentinal tubule occlusion by sonifying and reducing the particle size to less than one micron on average. Ultimately, this significantly enhances the depth to which the active ingredient can be deposed within the dentinal tubule.

The solution including the active ingredient (e.g., the "active ingredient solution"), such as an oxalic acid, potassium salt dihydrate solution, may be acidic. In one embodiment, the acidic solution has a pH ranging from about 1.0 to 6.0, or any sub-range therein. For example, the pH of the solution may be 1.0 to 5.0, 1.0 to 4.5, 1.25 to 4.5, 1.5 to 4.5, 1.25 to 4.0, 1.25 to 3.5, 1.25 to 3.0, 1.5 to 2.5, or 1.5 to 2.0, or others. The pH of the acidic solution may at least partially be controlled by the amount of active ingredient (e.g., potassium oxalate dihydrate) that is used in the formulation. Addition of potassium oxalate dihydrate will tend to lower the pH of the solution.

In operation, the use of the active ingredient solution may be a one step process to stop sensitivity to cold and air immediately. It may also be helpful as a diagnostic aid to assist the dentist in differentiating between reversible fluid flow in dentin and nonpulp inflammation and irreversible fluid flow which is results in pulp inflammation. In one embodiment, several drops (e.g., 3 to 6) of the active ingredient solution may be placed in a container (e.g., a Dappen dish). A small, sterile cotton pallet may be saturated with the solution, which may then be gently rubbed or dabbed onto the affected tooth area. In one embodiment, the solution may be applied for at least thirty seconds. The solution may be gently rubbed around the margin or over the crown cementum or exposed root surfaces and/or onto the exposed root of teeth which are sensitive to cold or air stimuli. No brushing of the product on the tooth surface is necessary, and neither is rinsing. After application, any remaining solution may be evaporated from the applied area, for example, using a gentle air dispersion. A frosty white surface may be formed by the application, which is an acid resistant mineral layer that stops or limits fluid movement or dentin hypersensitivity to cold and air stimuli.

The disclosed composition can be applied on prepared tooth structures, such as vital dentin, both before and after oral hygiene treatment for prophylaxis for cleaning and scaling. The composition may be used as a one-step replacement under all crowns and inlays with veneer preparation. It can also be used on the dentin of all cavity preparation for amalgam alloys, and resin composite restoration. The acid resistant film forming liner material can have bonding materials applied directly on its surface for binding restorative materials. It may also be applied on the tooth surface following a bleaching procedure, whether the procedure is done in a dentist's office or if the patient uses a home bleaching kit. In addition, the solution (e.g., potassium oxalate dihydrate solution) can be used as a diagnostic tool to differentiate between acute dentinal pain and chronic pulpual pain. Acute dentin pain is generally called a reversible tooth pain. To the dentist and patient, this means that there is a defect located within the substance of the dentin and not within the nerves within the dental pulp. The problem is reversible without any invasive endodontic treatment. Alternatively, chronic dental pain is an irreversible stimulus which indicates that the nerves of the dental pulpual are inflamed and must be removed by some sort of biomechanical endodontic instrumentation. The potassium oxalate dihydrate solution of the present disclosure provides a simple one-step diagnostic treatment that allows the dentist to discriminate reversible and irreversible dental pain. When a patient complains of pain to cold and air and there are no diagnostic features of radiographic presence of a periapical radiolucency, fractured tooth root, or other obvious clinical problems then the dentist may simply rub the potassium oxalate dihydrate of the present disclosure onto and around edges or cavosurface margins of the tooth restoration interface. If the patient reports an immediate cessation to dentinal pain, then the dentist may complete the diagnosis that the problem is fluid flow in the dentin or microleakage. This is confirmation of reversible pulp inflammation and may be treated by repair or restoration and not the removal of the pulp.

In order to explain the mechanism of action of the disclosed composition, the following is a description of the mode of action of the disclosed solution used in, for example, a restorative procedure. However, the mode of action may be similar for all applications. The active ingredient solution (e.g., potassium oxalate dihydrate solution) may initially serve to break down the smear layer and open the substrate of dentin, as well as enamel and cementum. Buffering occurs to the pH of the solution and as the reaction progresses, the pH of the solution moves toward neutrality. Simultaneously, calcium granular particles precipitate on the entire cavity surface in addition to any small physiological cracks, which are normally present in adult enamel and or cementum of the root surface. The particles may at least partially occlude the dentinal tubules in the tooth. For example, the particles may occlude or block at least 50% or more of the cross-sectional area of the tubules, such as at least 75%, 85%, 90%, or 95%. In some embodiments, the particles may completely or substantially completely (e.g., at least 99%) occlude/block the dentinal tubules. In embodiments where the active ingredient is potassium oxalate dihydrate, for example, the active ingredient may react with hydroxyapatite (e.g., $Ca_{10}(PO_4)_6(OH)_2$ or $Ca_5(PO_4)_3(OH)$) in the tooth to form a precipitate of calcium oxalate ($Ca(C_2O_4)$). This granular precipitate, when dried, forms an acid resistant lining layer that is chemically bound to the surface as well as into the dentinal tubules of the cavity. Once the granular crystals are formed, the barrier effect is immediately felt by the patient. To the unaided eye, there is a slightly whitish film that may be seen on the surface of the cavity and tooth.

As described above, the active ingredient solution is highly effective at occluding dentinal tubules and preventing fluid flow therein. However, some active ingredients, such as potassium oxalate dihydrate, may have a relatively low solubility in water (25.419 g/L at 20° C.). The active ingredient solution is most effective when all or substantially all of the active ingredient (e.g., potassium oxalate dihydrate) is in solution, rather than precipitated out. At 20° C., or at about room temperature, about 25.4 grams of potassium oxalate dihydrate will dissolve in one liter of water. However, if left for long periods of time, such as in a product container, the potassium oxalate dihydrate may eventually start to precipitate out. This may occur if a solution is prepared and bottled as a product and then sits idle for days, weeks, or months while waiting to be sent to stores or to customers or once purchased and before use. The solubility may become more of a problem if the solution is stored at or encounters low temperatures (e.g., below room temperature). At low temperatures, the active ingredient, such as potassium oxalate dihydrate, may precipitate out of solution, and at a faster rate.

Accordingly, it would be beneficial to the efficacy and to the storage of the solution if the solubility and/or solubility rate of the active ingredient could be increased. It has been discovered that the addition of sodium hydroxide (NaOH) may significantly increase the solubility of the active ingredient (e.g., potassium oxalate dihydrate) and also improve the solubility rate of the solution. Without being held to any particular theory, it is believed that the solubility improvements are a result of a manipulation of the solubility equilibrium via Le Châtelier's Principle and the common ion effect.

Similar to above, the mechanism described below is described with reference to potassium oxalate dihydrate as the active ingredient. However, the same or a similar mechanism may apply to other active ingredients. Potassium oxalate dihydrate, or $KH_3(C_2O_4)_2{\cdot}2H_2O$, may be broken down into its components as $KH(C_2O_4)$+$H_2(C_2O_4)$+$2H_2O$. Oxalate, or $(C_2O_4)$, may be abbreviated as Ox, and sodium hydroxide may be abbreviated as NaOH. When potassium oxalate dihydrate dissolves in water, the ionic formula is as follows:

$$KH_3(C_2O_4)_2\cdot 2H_2O + H_2O \rightarrow K^+_{aq} + 3H^+_{aq} + 2Ox^-_{aq} + H_2O_{(1)}$$

When NaOH is added, it reacts with protic acids to form a salt (sodium oxalate) and water. The simple reaction equation for this reaction is:

$$2NaOH + H_2(C_2O_4)_2 \rightarrow Na_2(C_2O_4) + 2H_2O$$

The full reaction equation and the ionic breakdown for this reaction are:

$$2NaOH + H_2(Ox) + KH(Ox) + H_2O_{(sol)} \rightarrow Na_2(Ox) + KH(Ox) + 2H_2O_{(1)} + H2O_{(sol)}$$

$$2Na^+_{aq} + 2OH^-_{aq} + 3H^+_{aq} + 2Ox^-_{aq} + K^+_{aq} \rightarrow 2Na^+_{aq} + 2Ox^-_{aq} + K^+_{aq} + H^+_{aq}$$

As a result, the net ionic change, product to reactants, is $2OH^-{}_{aq}$+$2H^+{}_{aq}$→$2H_2O_{(l)}$. Accordingly, the addition of two (2) moles of NaOH to a potassium oxalate dihydrate solution results in the production of two moles of water and one mole of sodium oxalate. Therefore, one mole of potassium oxalate dihydrate is broken down into one mole of sodium oxalate and one mole of potassium oxalate. This means that for every two moles of NaOH added, one mole of potassium oxalate dihydrate is removed/consumed, thereby reducing the concentration by one mole. The reaction from adding the NaOH shifts the equilibrium to the products by reducing common ions by two moles of protic hydrogens. This shifts the solubility equilibrium of potassium oxalate dihydrate further into solution, thus increasing the solubility. Accordingly, the chemical equilibrium established in the aqueous solution described is shifted such that it favors further dissolution of the potassium oxalate dihydrate.

In some applications the equilibrium reaction reduces the concentration of potassium oxalate dihydrate by one mole and increases the concentration of water by two moles. This effectively increases the solubility because the concentration of the solute is lessened, and the concentration of the solvent is increased. However, by starting the reaction with a higher concentration of potassium oxalate dihydrate than ultimately desired and reacting it with NaOH, the final product may have the desired concentration (e.g., more salt can be dissolved when NaOH is added, compared to the solution without the NaOH addition). Sodium hydroxide is a strong base (e.g., alkaline), and its sodium oxalate product provides a higher pH than that of potassium oxalate dihydrate. The acid-base equilibrium is therefore changed by the addition of alkalinity and drives the equation to the acid side. The change in acid-base equilibrium affects the solubility of potassium oxalate dihydrate by shifting the equilibrium to the ionized state, thereby driving potassium oxalate dihydrate into solution. As a result of the addition of NaOH, the solubility of the salt at a given temperature and concentration of the salt in solution is increased. The addition of NaOH therefore allows more potassium oxalate dihydrate to dissolve in solution, compared to potassium oxalate dihydrate alone in solution, while retaining the same concentration of the salt. Furthermore, the addition of NaOH may decrease the time it takes to dissolve the potassium oxalate dihydrate into solution at a given temperature and concentration.

With reference to FIG. 1, a flowchart 10 is shown for a method of preparing a solution including an active ingredient and a solubility enhancer, according to an embodiment. In step 12, water may be purified using any suitable method, such as distillation, reverse osmosis, or others. In one embodiment, the water may have a water purity of 1,000,000 to 5,000,000 resistance in ohms. Instead of purifying the water in step 12, water already having a suitable purity level may be acquired and utilized.

In step 14, the active ingredient may be added to the water to form a solution. In one embodiment, the active ingredient may be potassium oxalate dihydrate (or the non-hydrated composition). However, other compositions, such as those listed in Table 1 may also be used as the active ingredient (or combinations thereof). The active ingredient may be added in an amount sufficient to provide a desired concentration of the active ingredient, as described above. For example, potassium oxalate dihydrate may be added to provide a concentration of 0.25% to 25% weight to volume (e.g., g/L).

In step 16, a solubility enhancer may be added to the solution. In one embodiment, the solubility enhancer is sodium hydroxide, NaOH. In another embodiment, the solubility enhancer may be potassium hydroxide, KOH, or other hydroxide salts such as Li, Cs, Rb, Ca, Sr, or Ba. The solubility enhancer may be added in an amount sufficient to provide the solution with the desired level of solubility of the active ingredient, as described above. In one embodiment, at least 0.1 g/L of solubility enhancer may be added to the solution, for example, at least 0.3, 0.5, 1.0, 2.0, 3.0, 4.0, 5.0, 6.0 or more g/L. Stated as ranges, the solution may include from 0.1 to 6.0 g/L of the solubility enhancer, or any sub-range therein, such as 0.1 to 5.0 g/L, 0.1 to 4.0 g/L, 0.1 to 3.0 g/L, 0.1 to 2.0 g/L, 0.2 to 1.5 g/L, 0.3 to 1.5 g/L, 0.5 to 1.5 g/L, or about 1.0 g/L. For example, NaOH may be added at a concentration of about 1 g/L of potassium oxalate dihydrate solution. Steps 14 and 16 may be performed in any order, and not necessarily in the order shown in FIG. 1.

In step 18, the solution may optionally be heated (e.g., above room or ambient temperature) in order to increase the solubility and/or solubility rate of the active ingredient in the solution. The solution may be heated to a temperature of up to 100° C., such as 30° C. to 75° C. or 30° C. to 60° C. The addition of the solubility enhancer may reduce the temperature of or eliminate the heating step. However, the heating step 18 may still reduce the production time of the solution.

In step 20, the solution may be mixed to speed up the dissolution of the active ingredient. As described above, the mixing may include ultrasonic processing, for example at a frequency of about 16,000 Hz to about 20,000 Hz. In addition to mixing, the solution may be circulated, for example using a pumping system. A pumping system may be included if the ultrasonic processing is performed using an ultrasonic horn. If the solution is heated during step 18, the temperature of the solution may be maintained during the mixing step 20. In addition to, or instead of, ultrasonic processing, other suitable mixing methods may also be used. In one embodiment, a magnetic stirrer may be used to stir and agitate the solution. Similar to above, the order of steps 18 and/or 20 may vary from that shown in FIG. 1. For example, heating and processing may be performed after the active ingredient has been added but prior to the addition of the solubility enhancer.

In step 22, the solution including the active ingredient and the solubility enhancer may be packaged. In one embodiment, the solution may be packaged in bottles. Bottles of the solution may then be distributed to dentists or other oral care professionals. The solution may also be packaged for single use. For example, the solution may be packaged in small vials (e.g., several mL) or the solution may be applied to single-use applicators, such as cotton swabs (e.g., "Q-tips" or cotton balls). Alternatively, the solution may be applied directly after it is produced, without substantial packaging.

In at least one embodiment, the solubility enhancer may increase the solubility of the active ingredient (e.g., oxalic acid, potassium salt dihydrate) in water. As described above, oxalic acid, potassium salt dihydrate has a solubility in water of 25.419 g/L at 20° C. In one embodiment, the addition of the solubility enhancer may improve the solubility of the active ingredient to at least 26.0 g/L at 20° C. For example, the solubility may improve to at least 26.5, 27.0, 27.5, 28.0, 28.5, 29.0, 29.5, or 30.0 g/L at 20° C. Stated another way, the solubility of the active ingredient may be improved by at least a certain value per a certain amount of solubility enhancer at a certain temperature. For example, in one liter of water, the solubility may be improved by at least 2.0 g/L per 1.0 gram of solubility enhancer at 20° C. In one embodiment, the solubility may be improved by at least 2.5, 3.0, 3.5, 4.0, or 4.5 g/L per 1.0 gram of solubility enhancer at 20° C.

EXAMPLES

Figure 2:
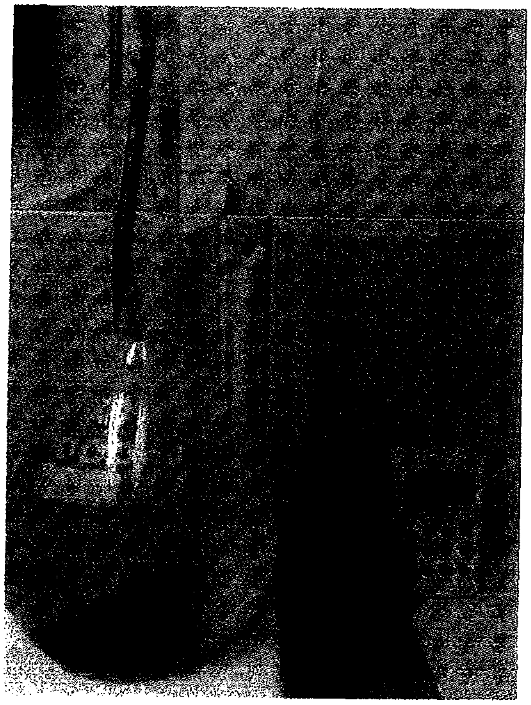
FIG. 2 is a solution of oxalic acid, potassium salt dihydrate being mixed.
Figure 3:
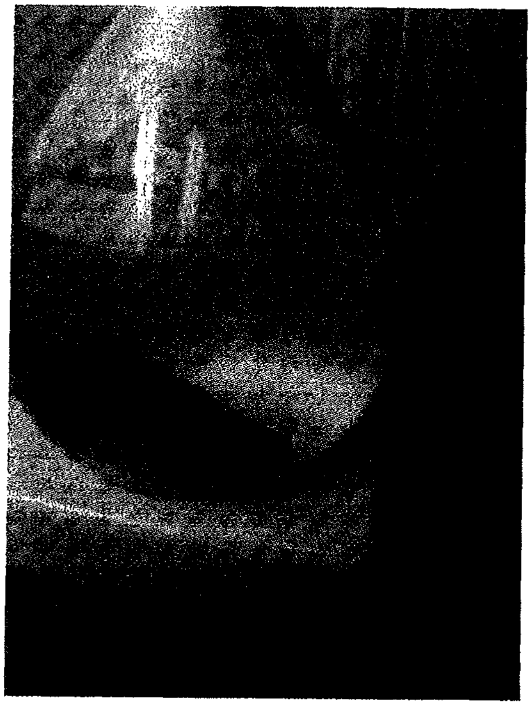
FIG. 3 is the solution of FIG. 2 with mixing stopped.

With reference to FIGS. 2-24, a solution of potassium oxalate dihydrate was prepared and mixed to demonstrate the improved solubility with the addition of NaOH. The starting solution of potassium oxalate dihydrate and water was prepared by adding 28.0 grams of potassium oxalate dihydrate to a one-liter (1 L) volumetric flask and filling the flask with one liter of 20° C. purified water (e.g., by reverse osmosis and/or micron filtration). The solution was mixed using a magnetic stirrer at a rate sufficient to form a vortex. After about 75 minutes of stirring at a temperature of 20° C., the solution was still cloudy, indicating that at least some of the potassium oxalate dihydrate was still undissolved. FIG. 2 shows the solution after 75 minutes with the stirrer in motion and FIG. 3 shows the solution after 75 minutes with the stirrer stopped.

Figure 4:
FIG. 4 is the solution of FIG. 2 with 1.0 gram of NaOH added and stirred for four minutes.
Figure 5:
FIG. 5 is the solution of FIG. 4 after 14 minutes of stirring.
Figure 6:
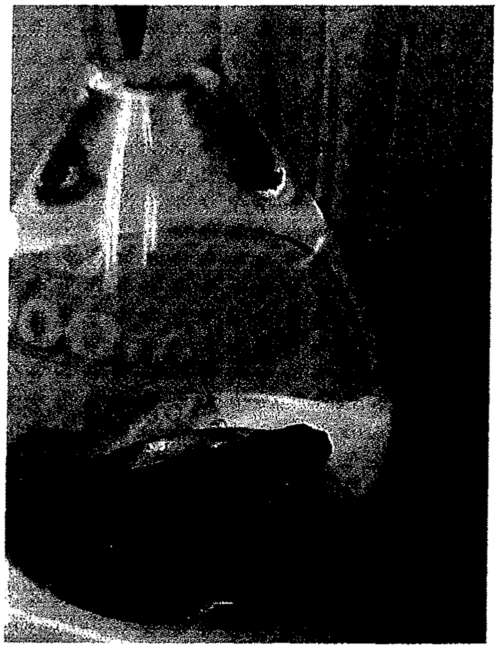
FIG. 6 is the solution of FIG. 4 after 14 minutes of stirring and with the stirring stopped.
Figure 7:
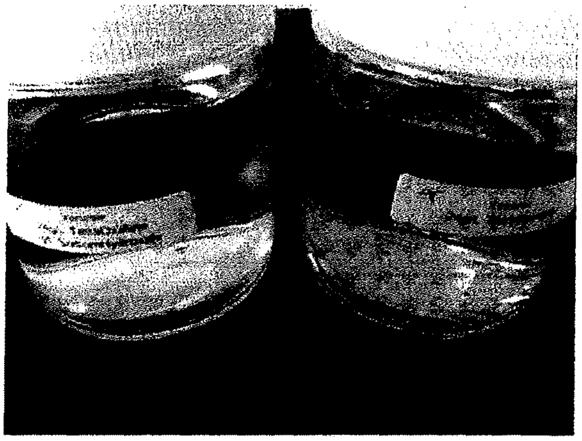
FIG. 7 is a pair of samples labeled alpha after 7 days at 9° C., including a variable sample having 24.0 g/L of oxalic acid, potassium salt dihydrate and 1.0 g/L of NaOH and a control sample having 24.0 g/L of oxalic acid, potassium salt dihydrate.
Figure 8:
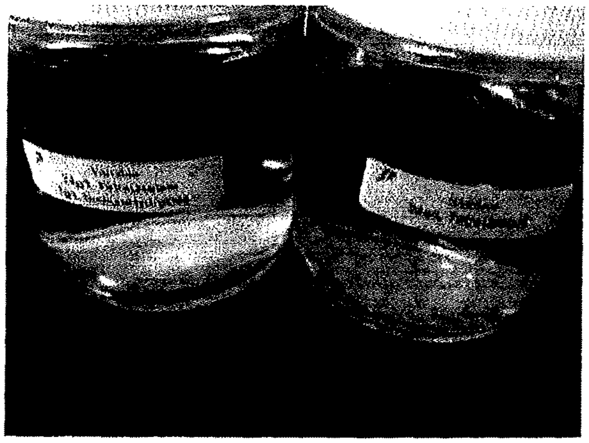
FIG. 8 is a pair of samples labeled beta after 7 days at 9° C., including a variable sample having 24.0 g/L of oxalic acid, potassium salt dihydrate and 1.0 g/L of NaOH and a control sample having 24.0 g/L of oxalic acid, potassium salt dihydrate.
Figure 9:
FIG. 9 is a pair of samples labeled gamma after 7 days at 9° C., including a variable sample having 24.0 g/L of oxalic acid, potassium salt dihydrate and 1.0 g/L of NaOH and a control sample having 24.0 g/L of oxalic acid, potassium salt dihydrate.
Figure 10:
FIG. 10 is a pair of samples labeled epsilon after 7 days at 9° C., including a variable sample having 24.0 g/L of oxalic acid, potassium salt dihydrate and 1.0 g/L of NaOH and a control sample having 24.0 g/L of oxalic acid, potassium salt dihydrate.
Figure 11:
FIG. 11 is a pair of samples labeled mu after 7 days at 9° C., including a variable sample having 24.0 g/L of oxalic acid, potassium salt dihydrate and 1.0 g/L of NaOH and a control sample having 24.0 g/L of oxalic acid, potassium salt dihydrate.

After the stirrer was stopped after 75 minutes of stirring, 1.0 gram of sodium hydroxide (NaOH) was added to the solution (1 L of water and 28.0 grams of potassium oxalate dihydrate) and stirring using the magnetic stirrer was resumed. After four (4) minutes of stirring, the solution was significantly less cloudy, as shown in FIG. 4. After 14 minutes of stirring, the solution was clear and free of solid crystals when observed with the naked eye, as shown in FIGS. 5 (stirring) and 6 (stirring stopped). These results confirm that at 20° C., 28.0 grams of potassium oxalate dihydrate would not fully dissolve in one liter of water, which was expected due to the solubility being 25.419 g/L at that temperature. However, with the addition of 1.0 gram of NaOH, the solubility increased rapidly. Significant improvement was observed after only several minutes, and complete dissolving occurred after 14 minutes.

With reference to FIGS. 7-25, solutions of potassium oxalate dihydrate and potassium oxalate dihydrate with sodium hydroxide were prepared to demonstrate the improved solubility rate with the addition of NaOH. Five pairs of control samples and variable samples (with NaOH) were prepared and labeled alpha ($\alpha$), beta ($\beta$), gamma ($\gamma$), epsilon ($\varepsilon$), and mu ($\mu$). The control sample solutions each included 24.0 g/L potassium oxalate dihydrate in purified water. The variable samples each included 24.0 g/L potassium oxalate dihydrate and 1.0 g/L NaOH in purified water. The control and variable samples were each 200 ml. The samples were initially mixed at room temperature such that there were no visible precipitates.

The pairs of solutions were then cooled to 9° C. and held at that temperature for about 7 days (168.5 hours) in a refrigerator and monitored by a certified thermometer. FIGS. 7-11 show the five pairs of samples at the end of the 7 days, with the variable sample on the left and the control sample on the right. As seen in the Figures, the variable samples had significantly fewer crystals form during the time at reduced temperature. After documenting the crystal formation, the sample pairs were stored at room temperature (approximately 20° C. to 24° C. during the experiment) and periodically observed to monitor the crystal dissolution. The endpoint for the experiment was the time after which full dissolution occurred.

Figure 12:
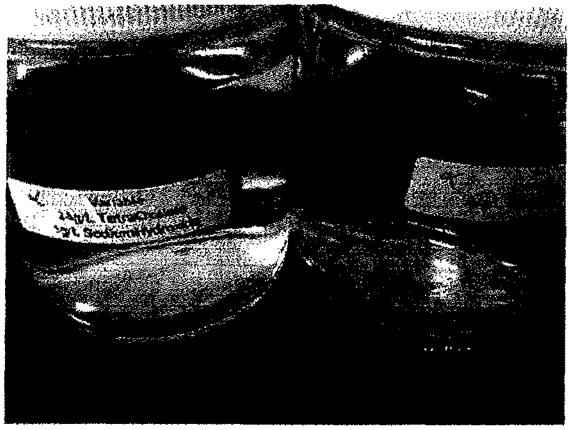
FIG. 12 is the alpha samples after 23 hours at room temperature.
Figure 13:
FIG. 13 is the beta samples after 23 hours at room temperature.
Figure 14:
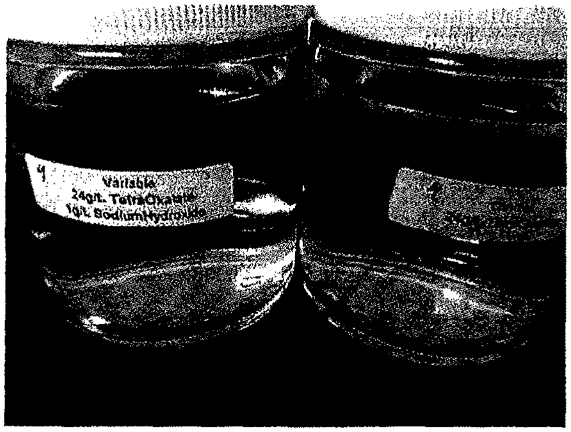
FIG. 14 is the mu samples after 23 hours at room temperature.
Figure 15:
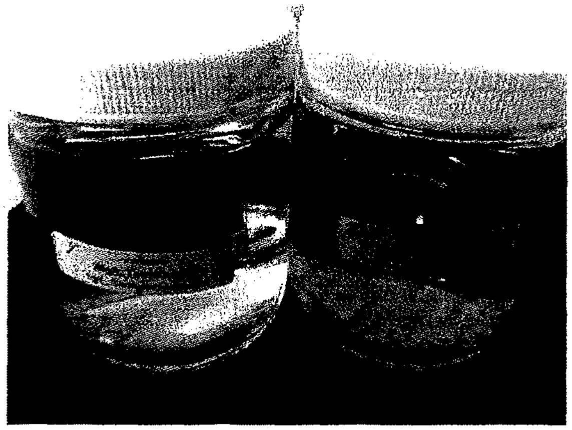
FIG. 15 is the gamma samples after 5 days at room temperature.
Figure 16:
FIG. 16 is the epsilon samples after 5 days at room temperature.
Figure 17:
FIG. 17 is the alpha samples after 5 days at room temperature.
Figure 18:
FIG. 18 is the beta samples after 5 days at room temperature.
Figure 19:
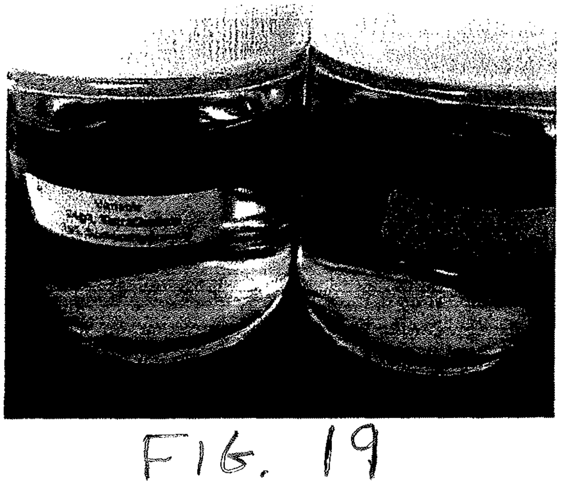
FIG. 19 is the mu samples after 5 days at room temperature.
Figure 20:
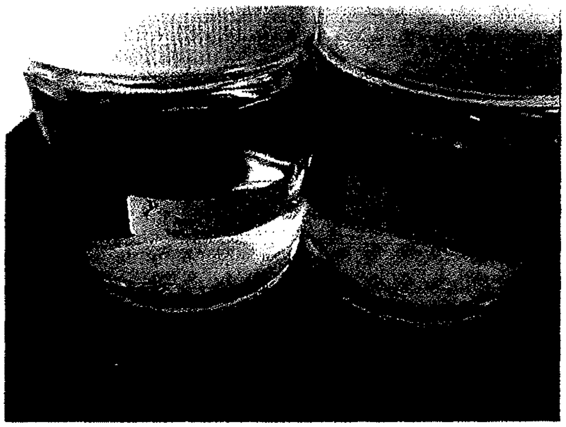
FIG. 20 is the gamma samples after 8 days at room temperature.
Figure 21:
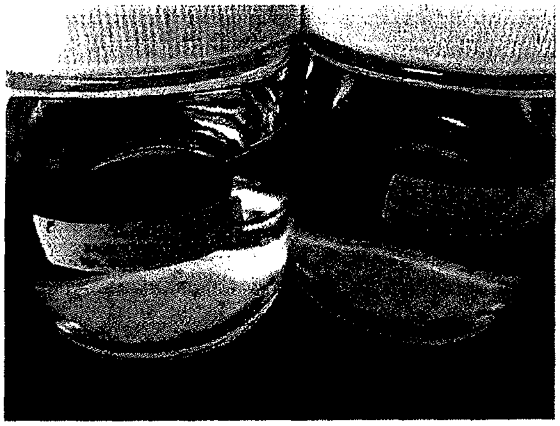
FIG. 21 is the epsilon samples after 8 days at room temperature.

In a little under one day (23 hours), the alpha, beta, and mu variable samples had reached full dissolution, as shown in FIGS. 12-14. The samples were observed again four days later, at which point variable samples gamma and epsilon had also reached full dissolution (FIGS. 15-16). It is not known when these samples reached full dissolution, and it may have been substantially sooner than the almost five days recorded, due to the gap in observation. At the time of full dissolution of the gamma and epsilon variable samples, all control samples still remained undissolved, as shown in FIGS. 15-19. The gamma and epsilon control samples were observed to have reached full dissolution after just over 8 days, as shown in FIGS. 20-21, and the alpha, beta, and mu control samples were observed to have reached full dissolution in just under 11 days, as shown in FIGS. 22-24.

A table including each sample's endpoint date and time, as well as days, hours, and total hours to endpoint, is shown in FIG. 25. The results of the experiment clearly showed that the addition of NaOH improved both the solubility and the solubility rate of the potassium oxalate dihydrate in solution. Less precipitation of potassium oxalate dihydrate crystals was observed in the variable samples when maintained at lower than room temperature, indicating an increase in solubility. Then, the crystals that formed in the variable samples fully dissolved back into solution in a significantly shorter amount of time compared to the control samples, indicating a faster solubility rate. Two of the variable samples were fully dissolved within one day, and the other three were likely fully dissolved much faster than the almost five days at which they were observed. Even with the gap in observation, the control samples still lagged well behind the variable samples in the time needed to fully dissolve. The first control samples did not fully dissolve for 8 days, with the remainder taking almost 11 days. Even considering the gap in observation, the control samples took an average of 173.6 hours longer to fully dissolve, compared to the variable samples having NaOH added thereto. Accordingly, the experimental data confirms that the addition of NaOH to a potassium oxalate dihydrate solution increases the solubility and the solubility rate of the potassium oxalate dihydrate.

Figure 26:
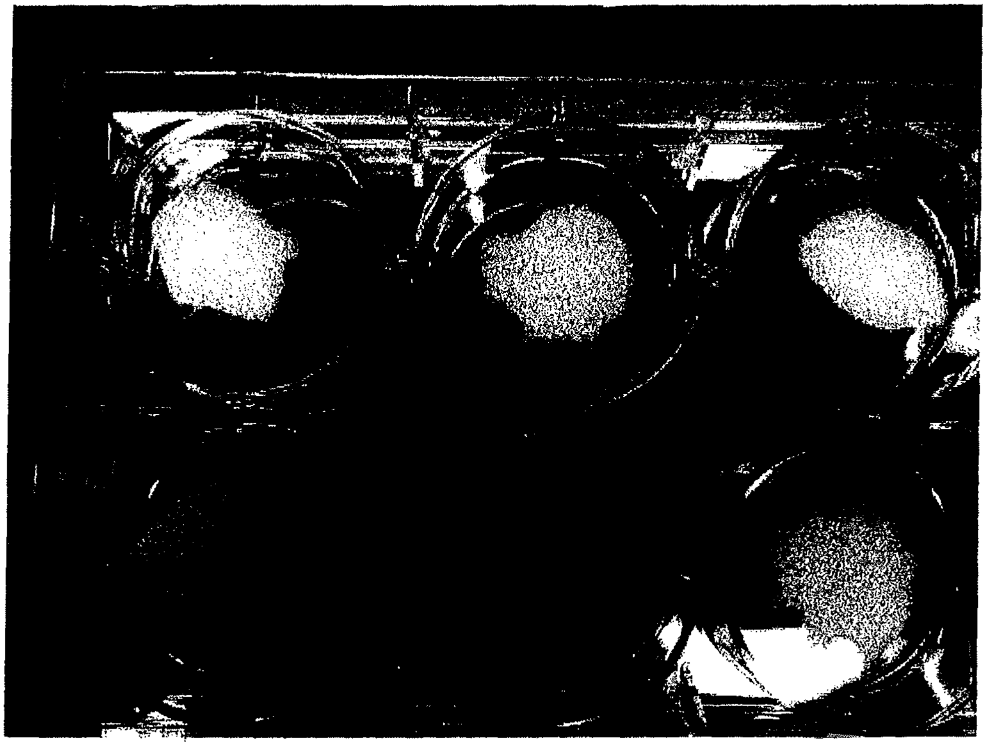
FIG. 26 is a set of samples testing the formation of crystals from a reaction between calcium and oxalic acid, potassium salt dihydrate with NaOH added.
Figure 27:
FIG. 27 is another set of samples testing the formation of crystals from a reaction between calcium and oxalic acid, potassium salt dihydrate with NaOH added.

With reference to FIGS. 26-27, experiments were performed to confirm the reaction between calcium and oxalic acid, potassium salt dihydrate with added sodium hydroxide to form crystals. Eight test samples were created, with the compositions listed in the table below:

| Sample Number | Composition |
|---|---|
| 1 | 40 g TOx with 4 g NaOH |
| 2 | 29.9 g TOx with 1 g NaOH |
| 3 | 28.6 g TOx with 1 g NaOH |
| 4 | 26.6 g TOx with 1 g NaOH |
| 5 | 24.0 g TOx with 1 g NaOH |
| 6 | 22.0 g TOx with 1 g NaOH |
| 7 | 20.0 g TOx with 1 g NaOH |
| 8 | 29 g TOx |

Accordingly, the samples include varying amount of oxalic acid, potassium salt dihydrate and one control sample without it (#8). Sample 1 has a larger amount of oxalic acid, potassium salt dihydrate and a larger amount of NaOH (4 grams, compared with 1 gram for #2-7). The samples were introduced into trays with a 10% calcium chloride solution. FIG. 26 shows the resulting precipitation of calcium oxalate crystals, with sample numbers 2, 1, and 8 from left to right on the top row and sample numbers 5, 4, and 3 from left to right on the bottom row. FIG. 27 shows samples 7 (left) and 6 (right). As can be seen in FIGS. 26 and 27, all of the samples, except #4, showed precipitation at least on par with the control sample. FIG. 4 appears to be a false negative, given that the samples with slightly greater and slightly less oxalic acid, potassium salt dihydrate both precipitated. Overall, the samples confirm that oxalic acid, potassium salt dihydrate combined with NaOH still react with calcium to create calcium oxalate ($Ca(C_2O_4)$) crystals.

Figure 28:
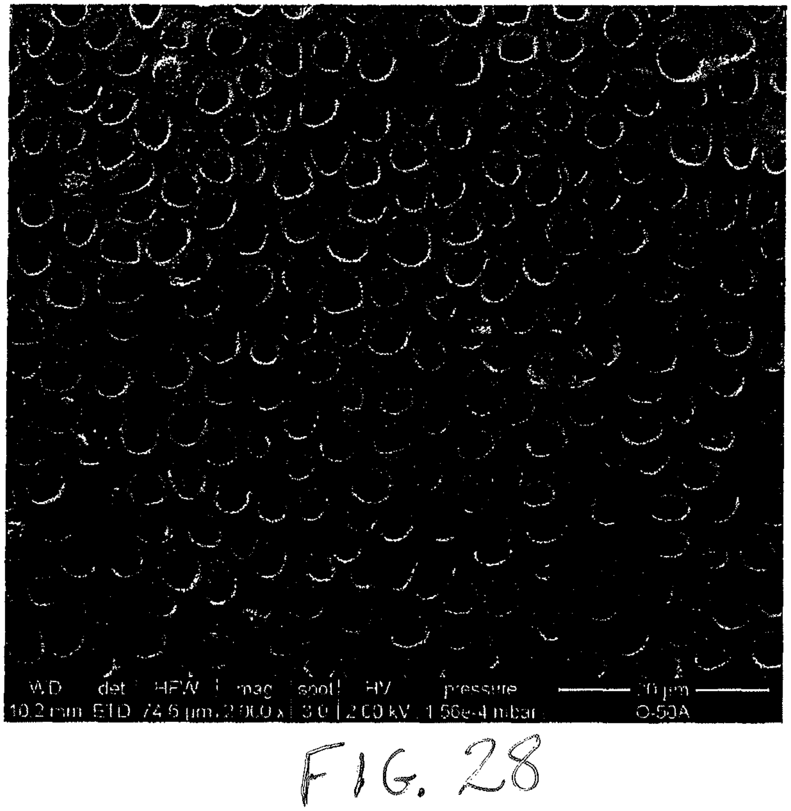
FIG. 28 is etched dentin showing unblocked dentinal tubules.
Figure 29:
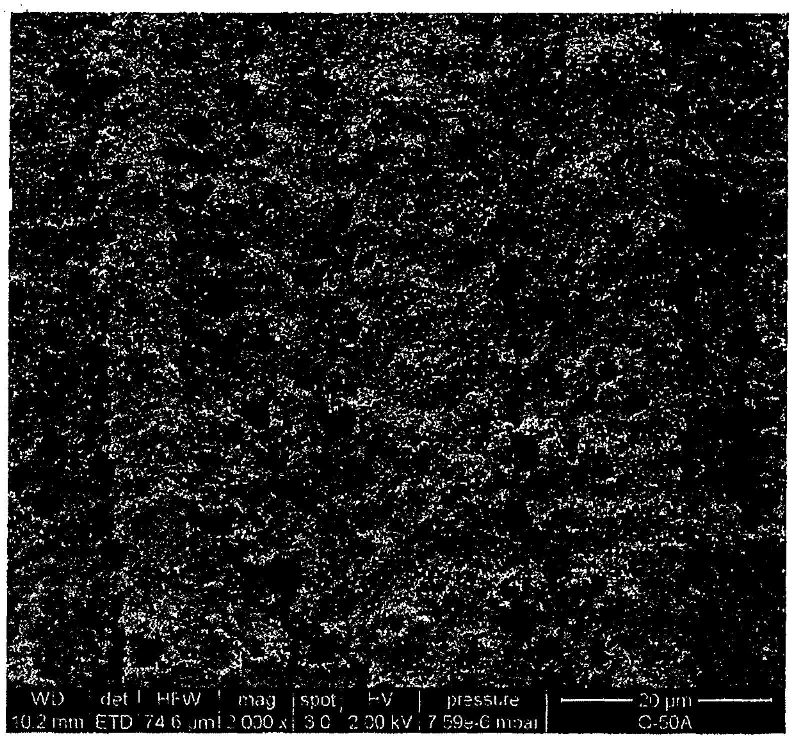
FIG. 29 is etched dentin after exposure to a solution including 40.0 g/L oxalic acid, potassium salt dihydrate and 4.0 g/L NaOH.
Figure 30:
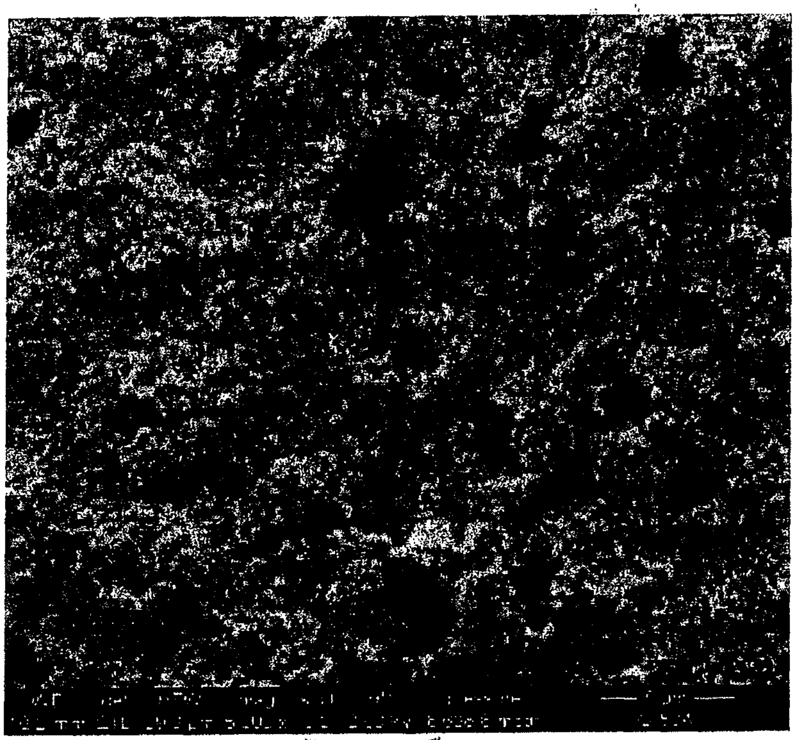
FIG. 30 is a higher magnification view of FIG. 29.
Figure 31:
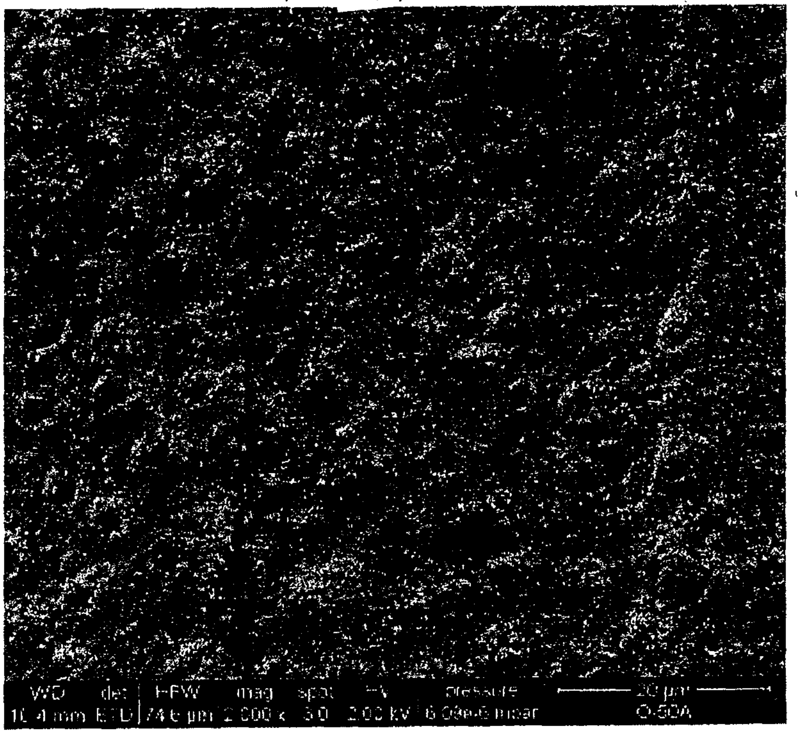
FIG. 31 is another region of etched dentin after exposure to a solution including 40.0 g/L oxalic acid, potassium salt dihydrate and 4.0 g/L NaOH.
Figure 32:
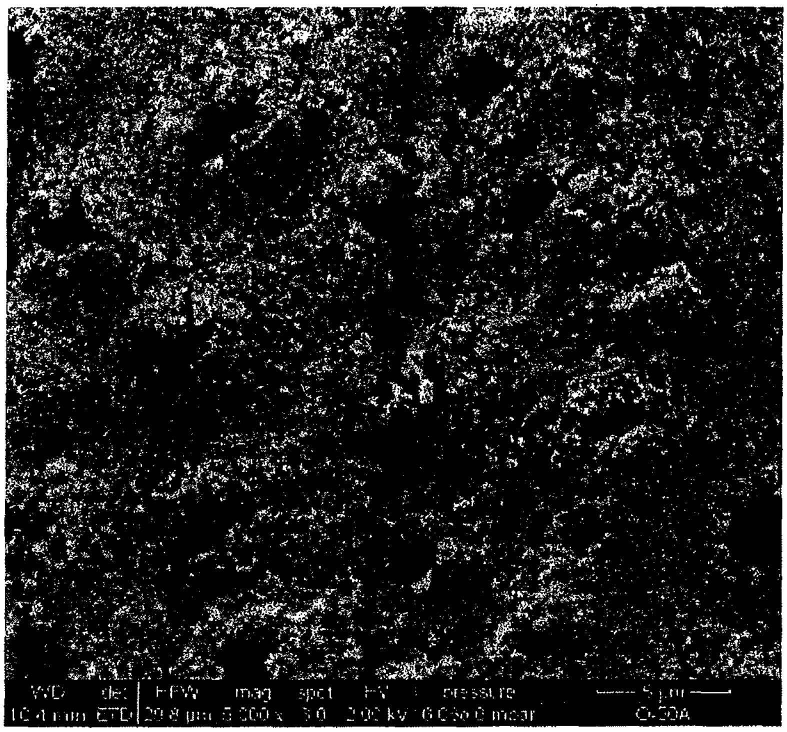
FIG. 32 is a higher magnification view of FIG. 31.

With reference to FIGS. 28-32, experimental results are shown that confirm that solutions of oxalic acid, potassium salt dihydrate combined with NaOH occlude dental tubules by forming calcium oxalate crystals. FIG. 28 shows a sample of etched dentin prior to the application of any solution. As can be seen, the tubules are open and unblocked. A sample of 40.0 g oxalic acid, potassium salt dihydrate combined with 4.0 g NaOH in one liter of purified water was applied to the etched dentin. FIGS. 29-32 show the resulting dentin surface at various magnifications. FIG. 29 shows the dentin at 2,000× magnification, and shows that the solution has coated the surface and the tubules are occluded with calcium oxalate crystals. FIG. 30 shows the dentin at the same location with a 5,000× magnification, showing several occluded tubules in more detail. FIGS. 31 and 32 are similar to FIGS. 29 and 30, but at a different location on the sample.

Experiments were performed to determine the change in solubility with the addition of a solubility enhancer (e.g., NaOH). A solution of 30 grams oxalic acid, potassium salt dihydrate and 1 gram of NaOH in 1 liter of purified water was prepared. The solution was maintained at 20° C. and mixed. The 30 grams of oxalic acid, potassium salt dihydrate did not fully dissolve, with approximately 0.08 grams remaining. Accordingly, this equates to a solubility of 29.92 g/L at 20° C., corresponding to an increase of 4.501 g/L compared to oxalic acid, potassium salt dihydrate alone (e.g., without NaOH). This increase was more than the value predicted based on the equilibrium equation, with the additional solubility believed to be attributed to Le Chatelier's Principle and the common ion effect.

Further experiments were performed to determine whether the increase in solubility from NaOH is linear or diminishing with increased amounts of NaOH. Since 1 gram of NaOH provided a solubility of ~29.9 g/L at 20° C. (a ~4.5 g/L increase), solutions with 34.40, 38.90, 43.40, and 47.90 grams of oxalic acid, potassium salt dihydrate were prepared with 2, 3, 4 and 5 grams of NaOH, respectively, in 1 liter of water. The solutions were maintained at 20° C. and mixed until all of the ingredients were dissolved or for two hours, whichever came first. The samples with 34.40 and 38.90 grams of oxalic acid, potassium salt dihydrate (2 and 3 grams of NaOH, respectively) dissolved completely. Accordingly, for additions of 1, 2, and 3 grams of NaOH, a linear relationship was found between solubility increase and amount of NaOH added. The sample with 43.40 grams of oxalic acid, potassium salt dihydrate and 4 grams of NaOH did not completely dissolve, with approximately 0.72 grams remaining undissolved after two hours. The sample with 47.90 grams of oxalic acid, potassium salt dihydrate and 5 grams of NaOH also did not completely dissolve, with about 3.8 grams of remaining. Accordingly, the relationship between amount of NaOH and increased solubility ceases to be linear somewhere between 3 and 4 grams of NaOH, and within that range, there begins to be diminishing returns.

Based on a trend line fit to the data, the addition of more NaOH may become ineffective between 5 and 6 grams.

Prophylaxis Paste Example: A sealing composition or dental desensitizing solution formed as described above and in accordance with the present invention, and containing a solubility enhancer formed as shown in FIGS. 2-24, may be integrated into a prophylaxis paste for reduction and/or elimination of dentine sensitivity. In accordance with the present invention, the desensitizing solution may advantageously be integrated within a dental or oral product to impart desensitizing effects to the product. A prophylaxis paste or prophy paste, as understood in the art, is typically employed to repair the enamel surface of a tooth. Oftentimes, the patient may have sensitivity associated with the repair and the dental work necessary to refurbish the tooth surface. To alleviate sensitivity, typical prophy paste may be mixed with the desensitizing solution as follows:

1. Provide the following constituents (by Fisher Chemical for example) by weight percent—70-90 wt. percent of glycerin; 10-29 wt. percent of desensitizing solution made as described herein; and 1-5% of pumice.
2. In a stainless-steel mixing vessel, combine the desensitizing solution with the glycerin, and begin mixing.
3. While mixing, heat the solution to a temperature within the range of 45 degrees Celsius to 88 degrees Celsius, until the solution is homogeneous.
4. Add pumice, and continue to heat and mix for at least one hour.
5. Turn off heat and mixing, and pour solution into a collection vessel.

It should be appreciated that the mixing method provided may be modified so long as a substantially homogeneous mixture of the solution is achieved.

The solubility enhancer may have manufacturing, stability, shipping, and processing benefits. During manufacturing, processing, or dispensing, if crystal formation occurs, application mechanisms can become plugged with the crystal buildup. The increased solubility will eliminate the likelihood of this occurrence because the solution is more soluble and able to handle a wider range of manufacturing temperatures and storage temperatures. The improved ease of re-dissolution, with or without aid, makes re-processing the solution take less time and energy.

To those points, and with reference to FIGS. 33-36, it can be seen that adding a solubility enhancer to a known desensitizer solution as described within U.S. Pat. Nos. 6,582,680, 6,500,407, and 6,458,339, each herein incorporated by reference in their entireties, enhances the inherent resistance within the desensitizer solutions of the present invention to form potassium tetraoxalate dihydrate crystals. Stated another way, the solubility enhancer within the present desensitizer solutions stabilizes the solutions to prevent crystal formation at relatively lower temperatures, and/or, to prevent crystal formation during relatively longer periods of shelf life.

Figure 33:
FIG. 33 is an aged sample of a composition similar to those of the present invention containing all but the solubility enhancer, wherein the composition has precipitated potassium tetraoxalate dihydrate crystals.

FIG. 33 is an aged sample of a composition similar to those of the present invention containing all but the solubility enhancer (see U.S. Pat. No. 6,582,680 for example) wherein after about five years on the shelf, the composition has during that time precipitated potassium tetraoxalate dihydrate crystals.

Figure 34:
FIG. 34 is a newer sample of the same composition of FIG. 33, wherein this newer composition has also precipitated potassium tetraoxalate dihydrate crystals.

FIG. 34 is a newer sample of the same composition of FIG. 33, wherein this newer composition has also been aged for about eight to nine months, and during that time has precipitated potassium tetraoxalate dihydrate crystals.

Figure 35:
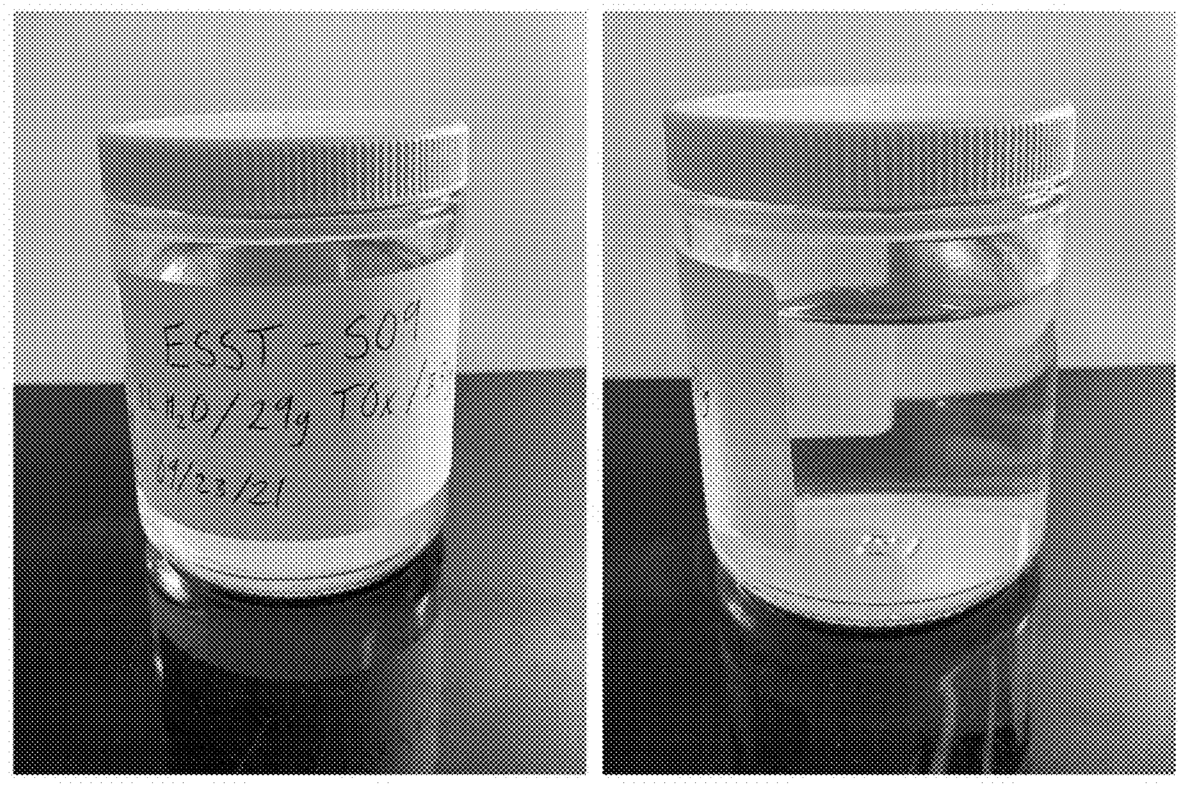
FIG. 35 is an aged sample of a composition formed in accordance with the present invention, containing the constituents of the composition of FIG. 34, but in addition also containing a solubility enhancer—no precipitate has formed.

FIG. 35 is an aged sample of a composition formed in accordance with the present invention, containing the constituents of the composition of FIG. 34, but in addition also containing a solubility enhancer such as sodium hydroxide—no precipitate has formed during the aging time.

Figure 36:
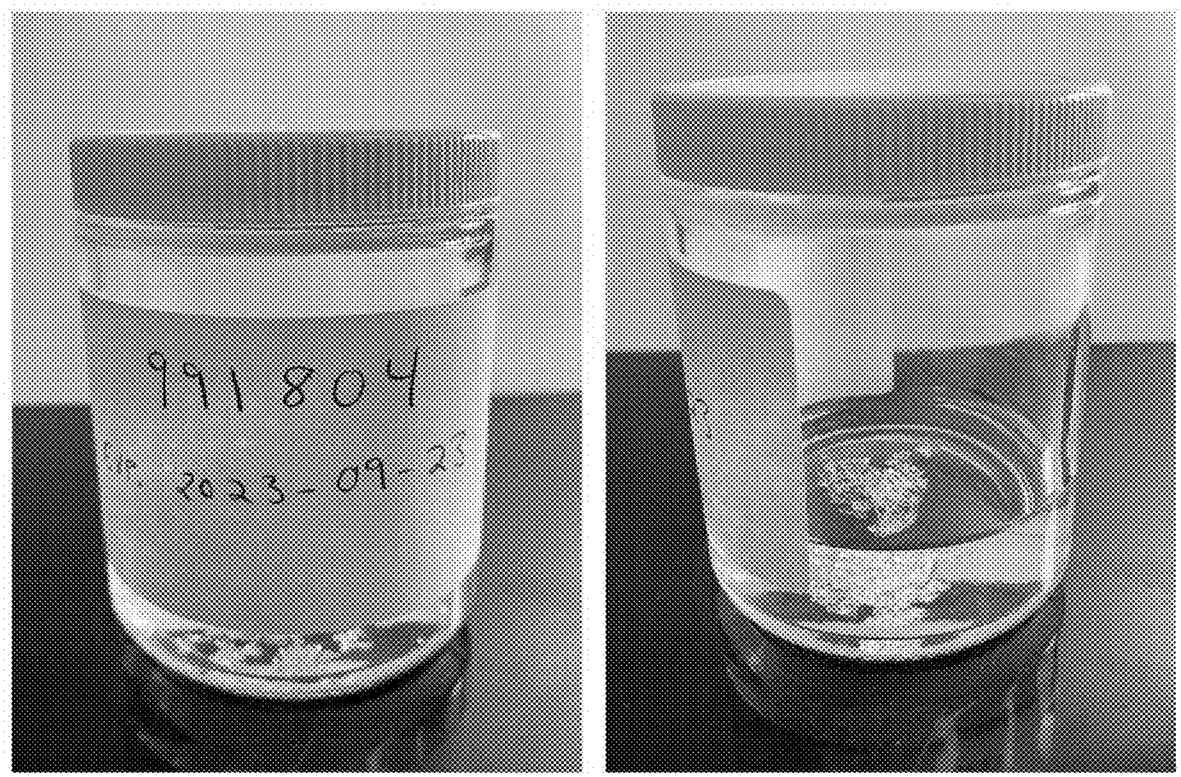
FIG. 36 is an identically aged sample of a composition identical to FIG. 35, except that no solubility enhancer is contained within the composition—the composition has precipitated potassium tetraoxalate dihydrate crystals.

FIG. 36 is an identically aged sample of a composition identical to FIG. 35, except that no solubility enhancer is contained within the composition (again, see U.S. Pat. No. 6,582,680)—the composition has precipitated potassium tetraoxalate dihydrate crystals.

Current studies indicate that a dentinal tubule can be effectively occluded with calcium hydroxyapatite, as a direct consequence of reacting a desensitizing solution of the present invention with the calcium from the tooth within the dentinal tubule. Stated another way, it is believed that the depth (D) of deposition of the calcium hydroxyapatite within the dentinal tubule when applied directly to the area in need of repair is substantially deeper than occlusion depth resulting from prior known desensitizing solutions.

Shipping temperatures can drop below solubility limits of the solution causing crystal formation. With the solubility enhancer the improved products of the present invention will be able to handle larger temperature variances and be able to return to its fully dissolved state once returned to normal temperatures, in the unlikely event of crystal formation during shipping, for example.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A dental desensitizing solution comprising: water; an active ingredient, the active ingredient, when applied to a tooth, being configured to react with calcium in the tooth to produce a plurality of acid-resistant crystals that at least partially occlude dentinal tubules in the tooth; and a solubility enhancer including sodium hydroxide (NaOH), the solubility enhancer increasing the solubility of the active ingredient in the solution, wherein said water and active ingredient are subjected to ultrasonic vibration using an ultrasonic cell disruptor, and, wherein said ultrasonic cell disruptor is a sonifier, and wherein vibration from the sonifier ranges from a frequency of about 16,000 Hz to about 40,000 Hz, and, wherein combination of the solubility enhancer with the use of the sonifier dramatically improves dentinal tubule occlusion by sonifying and reducing the particle size in solution to less than one micron on average.

2. The solution of claim 1, wherein the active ingredient includes an oxalic acid potassium salt.

3. The solution of claim 2, wherein the oxalic acid potassium salt includes oxalic acid, potassium salt dihydrate.

4. The solution of claim 1, wherein the solubility enhancer increases the solubility of the active ingredient by at least 1.0 g/L at a given temperature.

5. The solution of claim 1, wherein the solution includes at least 0.3 g/L of NaOH.

6. The solution of claim 1, wherein a pH of the solution is from 1.0 to 5.0.

7. The solution of claim 1, wherein the solution comprises from 0.1 to 6.0 g/L of the solubility enhancer.

8. The solution of claim 1, wherein the solution is an aqueous solution.

9. The solution of claim 1, wherein the active ingredient includes one or more of:

2-hydroxypropanedioic acid;

2-oxopropanedioic acid;

[(2-azanidylcyclohexyl) azanide; oxalic acid; platinum ($2^+$)];

tripotassium; chromium($3^+$); oxalate; hydrate (3:1:3:3);

tripotassium; chromium($3^+$); oxalate (3:1:3);

tripotassium; 2-bis[(carboxylatoformyl)oxy]stibanyloxy-2-oxoacetate; and

Oxotitanium ($2^+$) potassium ethanedioate hydrate (1:2:2:2).

10. A method of decreasing tooth sensitivity, comprising: applying a solution including water and an active ingredient and a solubility enhancer including sodium hydroxide (NaOH) to the tooth, the active ingredient being configured to react with calcium in the tooth to produce a plurality of acid-resistant crystals that at least partially occlude dentinal tubules in the tooth and the solubility enhancer being configured to increase the solubility of the active ingredient in the solution, wherein said solution is subjected to ultrasonic vibration, thereby reducing particle sizes therein to less than one micron on average.

11. The method of claim 10, wherein the solution is applied to at least one of the tooth dentin and cementum.

12. The method of claim 10, wherein the active ingredient includes an oxalic acid potassium salt.

13. The method of claim 12, wherein the oxalic acid potassium salt includes oxalic acid, potassium salt dihydrate.

14. The method of 12, wherein the solubility enhancer increases the solubility of the active ingredient to at least 26 g/L at 20° C.

15. A dental desensitizing solution consisting essentially of: an oxalic acid, potassium salt dihydrate as an active ingredient; and a solubility enhancer; wherein the solubility enhancer increases the solubility of the oxalic acid, potassium salt dihydrate in the solution to at least 26 g/L at 20° C., whereby said active ingredient is ultrasonically vibrated in solution, to a particle size less than one micron on average, to form said solution.

16. The solution of claim 15, wherein the solubility enhancer consists essentially of one member selected from the group consisting of NaOH, KOH, LiOH, CsOH, RbOH, $Sr(OH)_2$, $Mg(OH)_2$, $Ba(OH)_2$, or mixtures thereof.

17. The solution of claim 15, wherein the solution consists essentially of at least 0.3 g/L of the solubility enhancer.

18. The solution of claim 15, wherein a pH of the solution is from 1.0 to 5.0.

19. The solution of claim 15, wherein the solution consists essentially of 0.3 to 1.5 g/L of the solubility enhancer.

20. The solution of claim 15, wherein the solubility enhancer increases the solubility of the oxalic acid, potassium salt dihydrate to at least 28 g/L at 20° C.

21. A dental desensitizing solution consisting of: water; an active ingredient, the active ingredient, when applied to a tooth, being sized to react with calcium in the tooth to produce a plurality of acid-resistant crystals that at least partially occlude dentinal tubules in the tooth; and a solubility enhancer selected from one member from the group consisting of alkali metal hydroxides, alkaline earth metal hydroxides, and mixtures thereof, whereby said active ingredient is ultrasonically vibrated in solution, to a particle size less than one micron on average, to form said solution.

22. A method of decreasing tooth sensitivity, comprising: applying a solution including an active ingredient and a solubility enhancer to the tooth, the solubility enhancer selected from at least one of alkali metal hydroxides, alkaline earth metal hydroxides, and mixtures thereof, the active ingredient being sized to react with calcium in the tooth to produce a plurality of acid-resistant crystals that at least partially occlude dentinal tubules in the tooth and the solubility enhancer being configured to increase the solubility of the active ingredient in the solution, whereby said active ingredient is ultrasonically vibrated in solution, to a particle size less than one micron on average, to form said solution.

23. A dental desensitizing solution comprising: an active ingredient, the active ingredient, when applied to a tooth, being configured to react with calcium in the tooth to produce a plurality of acid-resistant crystals that at least partially occlude dentinal tubules in the tooth; and a solubility enhancer including sodium hydroxide (NaOH), the solubility enhancer increasing the solubility of the active ingredient in the solution, wherein the active ingredient includes one or more of:

2-hydroxypropanedioic acid;

2-oxopropanedioic acid;

[(2-azanidylcyclohexyl) azanide; oxalic acid; platinum ($2^+$)];

tripotassium; chromium($3^+$); oxalate; hydrate (3:1:3:3);

tripotassium; chromium($3^+$); oxalate (3:1:3);

tripotassium; 2-bis[(carboxylatoformyl)oxy]stibanyloxy-2-oxoacetate; and

Oxotitanium ($2^+$) potassium ethanedioate hydrate (1:2:2:2).

24. A method of forming a dental desensitizing solution consisting essentially of the following steps:

providing water in a flask;

adding to the flask an active ingredient selected from the group consisting of: [potassium oxalate dihydrate]; [2-(carboxymethoxy) maloic acid]; [ditartronic acid]; [isomalic acid, tartronate]; [tartronic acid]; [iminomalonate]; [mesoxalate]; [mesoxalic acid]; [dipotassium [(carboxylatocarbonyl)oxy](oxo)titanio oxalate]; [tripotassium bis[(carboxylatocarbonyl)oxy]stibanyl oxalate]; [trisodium 2-(carboxymethoxy)propanedioic acid]; [(2-azanidylcyclohexyl)azanide; oxalic acid; platinum(2+)]; 3-dexoyhexarate; [dipotassium; oxalate; platinum(2+); dihydrate]; [tripotassium; chromium(3+); oxalate; hydrate (3:1:3:3)]; [tripotassium; chromium(3+); oxalate (3:1:3)]; [tripotassium; 2-bis [(carboxylatoformyl)oxy] stibanyloxy-2-oxoacetate]; [potassium trioxalotoferrate (III)]; [potassium hydrogen ethanedioate zirconium (4:4:1)]; [potassium hydrogen ethanedioate hafnium (4:4:1)]; [oxotitanium (2+) potassium ethanedioate hydrate (1:2:2:2)]; [dipotassium oxalate titanium (4+) (2:3:1)]; [dipotassium; dioxoosmium (2+); oxalate]; [potassium chromium (III) oxalate trihydrate]; [potassium titanium oxide oxalate dihydrate]; [tripotassium 2,2',2",-[stibinetriltris (oxy)]tris(oxoacetate)]; [tetra potassium tertrakis[ethanedioato (2-)-kO1] halfnium]; [tetra potassium tertrakis[ethanedioato(2-)-kO1] zirconium]; [potassium hydrogen ethanedioate (1:3:2)]; [ethanedioate, potassium salt hydrate (1:1:2)]; [potassium ethanedioate hydrate (4:2:1)]; [potassium tetraoxalate]; [potassium tetraoxalate dihydrate]; [potassium trihydrogen dioxalate]; [2,3-dihydroxybutanedioic acid]; [2,3-dihydroxy-(2R,3R)-butanedioic acid monopotassium salt]; [potassium sodium tartrate]; [dipotassium tartrate];

[potassium sodium tartrate tetrahydrate]; [2-hydroxy-propanedioic acid]; [2-oxopropanedioic acid]; and mixtures thereof;

adding to the flask a solubility enhancer selected from one member from the group consisting of alkali metal hydroxides, alkaline earth metal hydroxides, and mixtures thereof;

heating the solution; and ultrasonically vibrating the solution with a sonifier to mix the solution and to result in active ingredient particles in solution having an average particle size less than one micron.

25. The method of claim 24 wherein the active ingredient is potassium oxalate dihydrate and the solubility enhancer is selected from the group consisting of NaOH, KOH, LiOH, CsOH, RbOH, $Sr(OH)_2$, $Mg(OH)_2$, $Ba(OH)_2$, and mixtures thereof.

26. The method of claim 24 wherein the active ingredient is potassium oxalate dihydrate and the solubility enhancer is NaOH.

27. The method of claim 24 wherein the active ingredient is added at 0.25 to 25 weight percent, and, the solubility enhancer is added at 0.1 to 0.5 weight percent of the total solution.

28. A dental desensitizing solution formed from the method of claim 24.

* * * * *